United States Patent [19]

Pettit et al.

[11] Patent Number: 4,986,988
[45] Date of Patent: Jan. 22, 1991

[54] ISOLATION AND STRUCTURAL ELUCIDATION OF THE CYTOSTATIC LINEAR DEPSIPEPTIDES DOLASTATIN 13 AND DEHYDRODOLASTATIN 13

[75] Inventors: George R. Pettit, Paradise Valley; Yoshiaki Kamano, Tempe, both of Ariz.

[73] Assignee: Arizona Board of Regents, Tempe, Ariz.

[21] Appl. No.: 353,960

[22] Filed: May 18, 1989

[51] Int. Cl.$^5$ ............... A01N 63/02; A01N 27/00; A61K 31/015
[52] U.S. Cl. ............... 424/520; 424/550; 514/183; 514/764; 514/765
[58] Field of Search ............... 424/95, 104; 514/764-765

[56] References Cited

U.S. PATENT DOCUMENTS

| | | | |
|---|---|---|---|
| 4,414,205 | 11/1983 | Pettit | 424/95 |
| 4,486,414 | 12/1984 | Pettit | 424/95 |
| 4,816,444 | 3/1989 | Pettit et al. | 514/17 |

OTHER PUBLICATIONS

"Isolation and Structure of the Cytostatic Depsipeptide Dolastatin 13 from the Sea Hare Dolabella Auricularia", Pettit et al., J. Am. Chem. Soc., 1989, 111, 5015-5017.

Primary Examiner—Merrell C. Cashion, Jr.
Assistant Examiner—C. Azpuru
Attorney, Agent, or Firm—Richard R. Mybeck

[57] ABSTRACT

The Indian Ocean sea hare Dolabella auricularia has been found to contain a new cell growth inhibitory and antineoplastic (P388 leukemia) cyclodepsipeptide designated dolastatin 13$^{(1)}$ and a companion substance dehydrodolastatin 13$^{(2)}$. A series of high field (400 MHz) 2D-NMR experiments including sequential analyses by HMBC and NOE techniques and tandem mass spectrometry provided structural determinations. Dolastatin 13 and dehydrodolastatin 13 represent a new class of cyclodepsipeptides. Pharmaceutical preparations and therapeutic regimens employing these new cytostatic depsipeptides are disclosed. The depsipeptides have the following structure:

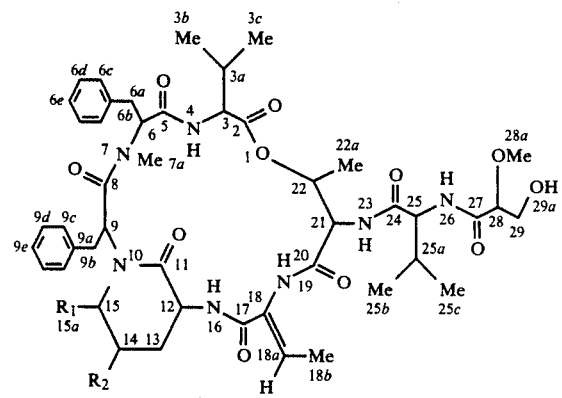

1: $R_1 = OH$; $R_2 = H$
2: $R_1 = R_2 = \Delta^{14,15}$

4 Claims, No Drawings

ISOLATION AND STRUCTURAL ELUCIDATION OF THE CYTOSTATIC LINEAR DEPSIPEPTIDES DOLASTATIN 13 AND DEHYDRODOLASTATIN 13

Financial assistance was provided by the National Cancer Institute PHS Grant CA-146049-05-12, DHHS Contract N01-CM-97262, NSF Grants CHE-8409644 and CHE-8620177 and numerous private foundations.

INTRODUCTION

The present invention relates to cytostatic linear depsipeptides herein denominated "Dolastatin 13" and "Dehydrodolastatin 13" which are obtained from the Indian Ocean shell-less mollusk *Dolabella auricularia;* to pharmaceutical preparations containing Dolastatin 13 and Dehydrodolastatin 13 as an essential active ingredient, and to methods of using such preparations to inhibit cell growth in a host afflicted therewith.

BACKGROUND OF THE INVENTION

The great Roman natural scientist Gaius Plinius Secundus (Pliny the Elder) in his comprehensive study, circa 60 AD, first described a most potent Indian Ocean sea hare of the genus Dolabella. (The Romans first designated Mollusca of the family Aplysidae as sea hares because of the similarity between the ears of a hare and the auriculate tentacles of these gastropods). However a consideration of the potential of the Indian Ocean Dolabella with respect to modern medical problems is only of recent origin. (See Pettit's U.S. Pat. Nos. 4,414,205, Nov. 8, 1983, Dolastatins 1-3; 4,486,414, Dec. 4, 1984, Dolastatins A and B; and 4,816,444, Mar. 28, 1989, Dolastatin 10).

The dolastatins may correspond to the potent *D. auricularia* constituents (See: 1969 Ph.D. dissertation of M. Watson. U. of Hawaii, "Some Aspects of the Pharmacology, Chemistry and Biology of the Midgut Gland Toxins of Some Hawaiian Sea Hares, especially *Dolabella auricularia* and *Aplysia pulmonica*", University Microfilms Inc., Ann Arbor, Mich.)

The biological properties exhibited by the *Dolabella auricularia* have been pursued for centuries but it was only in 1972 that this laboratory found Indian Ocean specimens of this captivating sea hare which yielded extracts that proved effective (over 100% increase in life span) against the U. S. National Cancer Institute's (NCI) murine P388 lymphocytic leukemia (PS system). Subsequently, this laboratory succeeded in isolating ten new (and powerful) cell growth inhibitory and/or antineoplastic peptides which were designated dolastatins 1 through 10, the nomenclature being based on the source of the substance and not on any similarity of chemical structure.

Of the early work, dolastatin 1 was found to be the most active (lowest dose) antineoplastic substance (33% cure rate against the NCI murine B16 melanoma at 11 µg/kg) known in its time. Because of the dolastatin's potency, the sea hare seems to require only vanishingly small quantities (about 1 mg each from 100 kg), making isolation and structural elucidation of these peptides exceptionally challenging. Later another substance was isolated and determined to be a unique linear pentapeptide and was denominated "dolastatin 10". This substance was the most important *Dolabella auricularia* antineoplastic constituent located as it appeared to be the most active (lowest dose) antineoplastic substance found up to that time. For instance, dolastatin 10 showed a 17-67% curative response at 3.25-26 µg/kg against the NCI human melanoma xenograft (nude mouse), 42-138% life extension at 1.44-11.1 µg/kg using the B16 melanoma and 69-102% life extension at 1-4 µg/kg against the PS leukemia ($ED_{50}=4.6\times10^{-5}$ µg/ml). Now dolastatin 13, a markedly different substance, has been found to be strongly active against the NCI's P388 lymphocytic leukemia (PS System) (See: Schmidt et al, *Experienta.* 1978, 34, 659-660) cell line with an $ED_{50}$ of 0.0013 µg/mL. The PS System is an excellent predictor of activity against various types of human neoplasms (See: Vendetti et al, *Lloydia*, 30, 332 et seq (1967) and references cited therein.) Dehydrodolastatin 13 exhibits similar properties.

BRIEF SUMMARY OF THE INVENTION

The present invention relates to the discovery of a new and potent cytostatic substance denominated "Dolastatin 13" which is extracted from the Indian Ocean shell-less mollusk *Dolabella auricularia* in the manner hereinafter described in detail. A related substance, namely, dehydrodolastatin 13 is also disclosed. The substance and its related substance, their synthetic counterparts and the non-toxic pharmaceutically active derivatives thereof can be formulated with pharmacologically acceptable carriers into useful pharmaceutical preparations having demonstrable and confirmable levels of cell growth inhibitory activity when measured by the generally accepted protocols in use at the United States National Cancer Institute.

Accordingly, a principal object of the present invention is to provide new agents useful in the retardation or growth inhibition of one or more types of malignant cells.

Another object of the present invention is to provide methods and procedures for isolating cell growth inhibitory substances from marine life in a form in which they may be readily and usefully employed in the therapeutic treatment and management of one or more types of neoplasms which occur in human hosts.

A further object of the present invention is to provide means and methods of creating useful pharmaceutical preparations for the treatment and management of neoplastic disease which preparations contain as their essential active ingredient a unique cytostatic factor obtained from the Indian Ocean shell-less mollusk *Dolabella auricularia*, its synthetic counterpart, or a non-toxic pharmaceutically active derivative thereof.

These and still further objects as shall hereinafter appear are readily fulfilled by the present invention in a remarkably unexpected manner as will be readily discerned from the following detailed description of an exemplary embodiment thereof.

DESCRIPTION OF THE PREFERRED EMBODIMENTS

The Organism

Taxonomy: *Dolabella auricularia* belongs to the family Aplysidae, the class Gastropoda and the phylum Mollusca. In a reference by H. Engel in "Zoologische Mededeelingen," Leiden, 24, 197-239 (1945), there are numerous color plates of specimens of Dolabella. Also in this reference is a listing of previously presumed different species of Dolabella which were later found to be the same and identified as *Dolabella auricularia.* These species are: *Dolabella agassizi, D. andersonii, D. hasseltii, D. hemprichii, D. neira, D. peronii, D. rumphii,*

D. *teremidi*, D. *tongana*, D. *truncata*, D. *variegata*, and D. *scapula*.

In appearance, the Dolabella used herein were olive green in color having a pear-shaped body and average length, 15-20 cm. The reference by H. Engel has detailed descriptions of Dolabella collected around the world.

The Dolabella collection site used for initial isolation of the dolastatins was on the eastern side of Mauritius in the Indian Ocean, approximate location, 21 S latitude, 56 E longitude, in 4-5 ft. deep water off the coast of the island.

Another site where Dolabella can be collected is near Negros Island in the Philippines, approximate location 9 N latitude, 123 E longitude. Extracts of Dolabella species from five separate collections all contained antineoplastic activity.

Isolation and Purification

A variety of methods can be used to isolate and purify dolastatin 13 and dehydrodolastatin 13 from samples of sea hare, such as, solvent extraction, partition chromatography, silica gel chromatography, preparative thin-layer chromatography, and crystallization from solvents.

Isolation of Dolastatin 13

A combined ethanol-2-propanol extract of D. *auricularia* (1,000 kg. wet, collected in 1982) was concentrated to an active methylene chloride fraction by a series of solvent partition steps. Extensive column chromatographic separation (steric exclusion and partition on Sephadex ®, partition and adsorption on silica gel and HPLC) using gradient elution techniques guided by PS bioassay led to 25.2 mg of pure dolastatin 13, ($2 \times 10^{-7}$% yield, from 1000 kg of wet sea hare).

A pure specimen of dolastatin 13 was obtained as crystals from methylene chloride-hexane 10.6 mg, $6 \times 10^{-8}$% yield): mp 286°-289° C.; $[\alpha]_D + 94°$ (c=0.01, $CH_3OH$); $R_f 0.56$ in 90:10:0.8 $CH_2Cl_2$—$CH_3OH$—$H_2O$; see scheme 1 for mass spec.; UV ($CH_3OH$) $\lambda_{max}$ (log $\epsilon$), 220 (3.04) nm; and IR (NaCl plate $\nu_{max}$ 3384, 3315, 2960, 2930, 1733, 1677, 1653, 1529, 1205, 750 and 700 cm$^{-1}$.

Based on results of detailed high field (400 MHz) $^1$H- and $^{13}$C-NMR and high resolution SP-SIMS peak matching, molecular formula $C_{46}H_{63}H_7O_{12}$ was deduced for dehydrolastatin 13. A combination of $^1$H, $^1$H-COSY, $^1$H, $^{13}$C-COSY and $^1$H, $^1$H-relayed COSY experiments indicated eight discreet spin coupled systems of which four corresponded to the well known amino acids threonine (Thr), N-methyl-phenylalanine (MePhe), and valine (Val, two units). Threonine and the two valine units were also detected by amino acid analyses of the products from acid-catalyzed (6N HCl, 110° C., 24 h) hydrolysis. Assignment of the fifth and sixth units as an N,N-disubstituted phenylalanine was realized by NMR interpretations. From a series of double and triple relayed coherence transfer experiments (homonuclear relay) and sensitivity enhanced heteronuclear multiple bond correlation experiments (HMBC), the latter Phe derivative was found to be the new cyclic hemiacetal 3-amino-6-hydroxy-2-piperidone (Ahp), presumably derived from a Phe-Glu dipeptide precursor. (Glu-$\gamma$-carboxyl-aldehyde).

Continuation of the NMR experiments led to assignment of the seventh unit as the rare dehydro amino acid, $\alpha,\beta$-dehydro-2-aminobutanoic acid (cis-Abu), presumably from dehydration of Thr, and the eighth, as 2-O-methyl-glyceric acid (MeGlc). Because of some ambiguity the Abu olefin was only tentatively assigned the Z-configuration shown. Confirmation for the Abu and MeGlc assignments was obtained from results of the HMBC experiment. Initial attempts at sequencing dolastatin 13 using nOe data proved unsuccessful presumably due to a folded solution conformation and the small magnitude of the observed nOes. The correct sequence of units was achieved using HMBC, and by combining the results from experiments in two different solvents (See: Table 1 below). With dichloromethane-$d_2$ as solvent, several segments of dolastatin 13 were established, but due to overlapping signals in the carbonyl region it was necessary to use data obtained in pyridine-$d_5$, where only two carbonyl chemical shifts overlapped. The only assumption made to complete the overall structure was that the carbonyl group at 174.38 ppm correspond to an ester and must therefore be attached to the Thr oxygen. The resultant structure as shown immediately below, was confirmed by the sequence determination shown in Scheme 1 and tandem mass spectrometry. The structure for dolastatin 13 is:

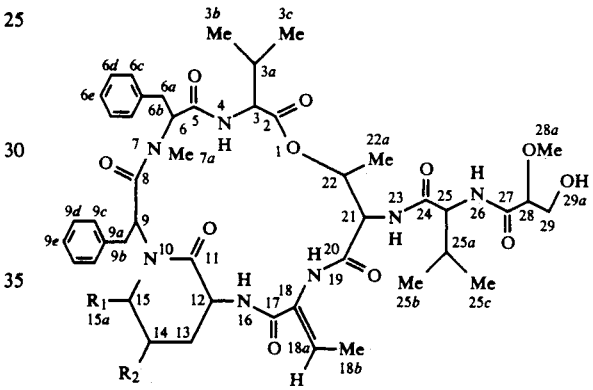

wherein: $R_1 = OH$; $R_2 = H$

Isolation of Dehydrodolastatin 13

A small (1.72 g) albeit PS active, fraction was prepared from 1600 kg (wet wt) of D. *auricularia* collected in the Indian Ocean (East Africa). The fraction was further separated (PS bioassay) by gradient HPLC (RP8 silica gel, 1:1 methanol-water→100% methanol as mobile phase) to afford dolastatin 13 as reported above.

Dehydrodolastatin 13 was thereafter obtained as a minor component together with dolastatin 13 from the same fraction; crystals from methylene chloride-hexane (0.74 mg, $4 \times 10^{-9}$% yield): mp 127°-132° C.; $[\alpha]_D + 38°$ (c=0.005, $CH_3OH$); $R_f 0.64$ (in preceding solvent system); HRSP-SIMS $[M+H]^+$ 888.4492, calcd. 888.4508 for $C_{46}H_{62}N_7O_{11}$; UV ($CH_3OH$)$\lambda$max (log $\epsilon$), 220 (3.11) nm; and IR (NaCl plate):$\nu_{max}$ 3382, 3311, 2960, 2930, 1732, 1678, 1653, 1530, 1467, 1202, 750 and 700 cm$^1$.

Based on results of detailed high field (400 MHz) $^1$H- and $^{13}$C-NMR and high resolution SP-SIMS peak matching, molecular formula $C_{46}H_{61}H_7O_{11}$ was deduced for dehydrodolastatin 13. A combination of $^1$H, $^1$H-COSY, $^{13}$C-COSY and $^1$H, $^1$H-relayed COSY (See: Bax et al, *J. Magn. Res.*, 61, 306-320 (1985)) experiments were employed to assign the structure to dehydrodolastin 13 as described above with respect to dolastatin 13.

Once the structure of dolastatin 13 was in hand it was clear from the combined NMR and mass spectral studies, that dehydrodolastatin 13 was the Ahp dehydration product of dolastatin 13 and corresponding to the structure shown below. The $^1$H- and $^{13}$C-NMR spectra the two depsipeptides appeared almost identical, with exception of the Ahp signals, and the amide proton of Val-2 at 7.42 (H-4) which upon dehydration shifts upfield by 1 ppm. The latter shift indicates hydrogen bonding between H-4 and O-15 in dolastatin 13. The structure elucidated for dehydrodolastatin 13 is:

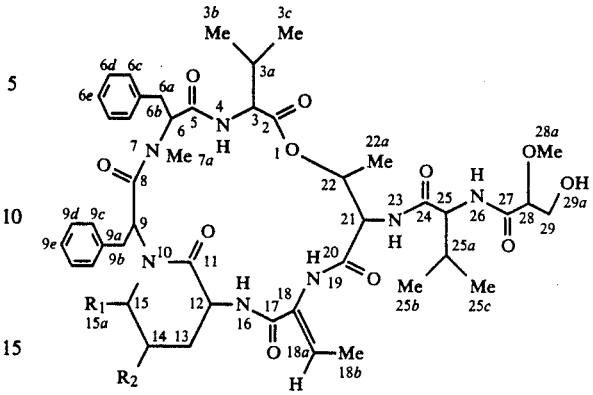

wherein: $R_1 = R_2 = \Delta^{14,15}$.

TABLE 1

$^1$H and $^{13}$C nmr assignments and selected nOe's for dolastatin 13 in CD$_2$Cl$_2$ solution and HMBC correlations from CD$_2$Cl$_2$ and C$_5$D$_5$N solutions.*

| # | $^{13}$C (mult.) | $^1$H (mult., J (Hz)) | NOE's | HMBC |
|---|---|---|---|---|
| Val$_2$ | | | | |
| 2 | 174.38 | | | |
| 3 | 59.05 | 4.18 t, 7.5 | | 2, 3a, 3b, 3c, 5 |
| 3a | 30.93 | 2.02 oct, 6.8 | 4 | 3, 3b, 3c |
| 3b | 19.26 | 0.92 d, 6.7, 3H | | 3, 3a, 3c |
| 3c | 19.59 | 0.95 d, 6.9, 3H | | 3, 3a, 3b |
| 4 | | 7.42 | 3a | 5, 6 |
| MePhe | | | | |
| 5 | 171.86 | | | |
| 6 | 62.39 | 5.28 | | 5, 6a, 6b |
| 6a | 34.14 | 3.85 dd, 14.0, 2.8 | 6 | |
| | | 2.81 dd, 14.0, 11.5 | 6, 6c | 6, 6b, 6c |
| 6b | 137.96 | | | |
| 6c | 129.72 | 7.35 | | 6a, 6d, 6e |
| 6d | 129.31 | 7.36 | | 6b, 6c |
| 6e | 127.55 | 7.26 | | 6d |
| 7b | 31.69 | 2.89 s, 3H | | 6, 8 |
| Phe | | | | |
| 8 | 172.49 | | | |
| 9 | 51.46 | 5.07 dd, 11.2, 5.0 | 9a, 9c, 15 | 8, 9a, 9b, 11, 15 |
| 9a | 35.27 | 2.93 dd, 14.6, 11.2 | 9c, 15 | 8, 9, 9b |
| | | 2.09 dd, 14.6, 4.8 | | 9, 9b |
| 9b | 136.28 | | | |
| 9c | 129.55 | 6.84 dd, 7.7, 2.1 | 9, 9a, 15 | 9a, 9d, 9c |
| 9d | 128.69 | 7.24 | | 9b, 9c |
| 9e | 127.30 | 7.23 | | 9d |
| Ahp | | | | |
| 11 | 171.86 | | | |
| 12 | 49.52 | 4.05 | | 11 |
| 13 | 22.21 | 2.21 dq, 3.0, 14.6 | 15, 16 | 11, 12, 14, 15 |
| | | 1.68 | | |
| 14 | 29.80 | 1.85 ddd, 14.0, 5.0, 2.6 | | 12 |
| | | 1.59 | | |
| 15 | 75.85 | 5.22 | 9, 9a, 9c, 12 | 11, 13 |
| 15a | | 3.98 | | |
| 16 | | 7.12 d, 9.5 | 19 | 12, 17 |
| ΔAbu | | | | |
| 17 | 163.78 | | | |
| 18 | 129.53 | | | |
| 18a | 134.15 | 6.76 br q, 7.0 | | 17, 18b |
| 18b | 13.24 | 1.66 d, 7.0, 3H | 19 | 17, 18, 18a, 20 |
| 19 | | 7.99 br s | 16, 21, 23, 29 | 20 |
| Thr | | | | |
| 20 | 169.94 | | | |
| 21 | 55.40 | 4.90 d, 10.4 | 22b | 20, 22, 22b, 24 |
| 22 | 73.96 | 5.24 | 3 | |
| 22a | 21.06 | 1.41 d, 6.8, 3H | 21 | 21, 22 |
| 23 | | 6.72 d, 10.4 | 19, 26 | 24 |
| Val$_1$ | | | | |
| 24 | 172.56 | | | |
| 25 | 61.93 | 4.01 | | 24, 25a, 25b |
| 25a | 29.59 | 2.41 oct, 6.9 | 23, 26 | 24, 25, 25b, 25c |
| 25b | 19.42 | 1.13 d, 6.9, 3H | | 25, 25a, 25c |

TABLE 1-continued $^1$H and $^{13}$C nmr assignments and selected nOe's for dolastatin 13 in $CD_2Cl_2$ solution and HMBC correlations from $CD_2Cl_2$ and $C_5D_5N$ solutions.*

| # | $^{13}$C (mult.) | $^1$H (mult., J (Hz)) | NOE's | HMBC |
|---|---|---|---|---|
| 25c | 19.82 | 1.11 d, 6.9, 3H | | 25, 25a, 25c |
| 26 | | 7.38 | 25a, 25b | 25, 25a, 27 |
| MeGlc | | | | |
| 27 | 172.82 | | | |
| 28 | 83.43 | 3.74 t, 1.8 | 28b | 27, 28b |
| 28a | 58.23 | 3.38 s, 3H | 28 | 28 |
| 29 | 63.09 | 4.01 | | |
| | | 3.63 ddd, 12.0, 4.7, 1.8 | 29b | 27, 28 |
| 29b | | 4.42 t, 5.1 | 19, 29 | 29 |

*where no multiplicity is noted, it could not be determined due to overlapping signals.
\# Chemical shift values are interchangeable.

To further assist in the understanding of the present invention, a more detailed description of the experimental procedures now follows.

General Methods. Solvents used for chromatographic procedures were redistilled. The Sephadex ® LH-20 (25-100 u) employed for gel permeation and partition chromatography was obtained from Pharmacia Fine Chemicals AB, Uppsala, Sweden. Gilson FC-220 race track and FC-80 micro-fractionators connected to Gilson HM UV-visible Holochrome detectors were used for chromatographic fractionation experiments. Column chromatographic procedures with silica gel utilized the 70-230 mesh or silica gel 60 prepacked columns supplied by E. Merck (Darmstadt). A Partisil M9 10/50 ODS-2 (C-18 reverse phase) column (9.4 mm i.d. × 500 mm) was used for HPLC and obtained from Whatman, Inc. Clifton, N.J. Preparative layer plates were also obtained from Whatman, Inc. and the silica gel GF Uniplates for TLC were supplied by Analtech, Inc., Newark, Del. The TLC plates were viewed with UV light, developed with an anisaldehyde-acetic acid-sulfuric acid spray (heating at approx. 150° C. for 10 min) or with ceric sulfate-sulfuric acid (heating for 10 min).

Amino acid analyses were performed with a Beckman Model 121 unit. Ultraviolet spectra were recorded using a Hewlett-Packard 8450A UV/VIS spectrophotometer equipped with a HP7225A plotter. The infrared spectra were recorded with a Nicolet MX-1 FT instrument. High resolution SP-SIMS mass spectra were obtained using V.G. Analytical MM ZAB-2F and Kratos MS-50 triple analyzer mass spectrometers. High resolution electron impact mass spectra (m/ m 10,000) were recorded on Kratos MS-80 and MS-50 instruments, along with CAD spectra. Gas chromatography-mass spectrometry (GC-MS) of suitable derivatives was performed with a J & W fused silica DB-5 (0.243 mm × 30 m) column. Successive GC-MS procedures employed chemical ionization (m/ m 1,000, reagent $NH_3$), low resolution (m/ m 1,000) and high resolution (m/ m 3,000) electron impact methods. The NMR experiments (in various solvents using a Bruker 5-mm $^1$H $^{13}$C dual switchable probehead) were conducted using a Bruker AM-400 narrow bore spectrometer with an ASPECT 3000 computer and pulse programmer operating at 400.13 and 100.62 MHz for $^1$H- and $^{13}$C-NMR, respectively.

Animal Collection, Extraction, and Preliminary Experiments. The Western Indian Ocean (Mauritius) sea hare *Dolabella auricularia* was initially collected in October 1972. By March 1975 confirmed activity of an ethanol extract against the National Cancer Institute's (NCI) P388 lymphocytic leukemia (PS system) was established and showed T/C 235 at 600 mg to 167 at 176 mg/kg. A series of analogous extracts from subsequent recollections of the sea hare gave comparable results. The experiments reported herein were conducted with a 1982 recollection (same site) preserved in ethanol. The total volume of animal (1,000 kg) and ethanol preservative was 700 gallons.

After extraction and solvent partitioning 2.75 kg of methylene chloride concentrate was obtained for large-scale preparative HPLC. Two columns in series (6" × 10') were packed with silica gel (Davisil 633, 200-400 mesh, slurry packed in 7:3 hexane-ethyl acetate). The 2.75 kg of dark (green-black) concentrate was dissolved in ethyl acetate (2 gal) and pumped onto the column and chromatographed using the following solvent gradients at a rate of 60-72 l/h.

| Eluant | Eluant Vol. (l) | Fraction No. | Fraction Residue (g) |
|---|---|---|---|
| 70/30 hexane:ethyl acetate | 200 | 1 | 64.9 |
| 60/40 hexane:ethyl acetate | 120 | 2-8 | 282 |
| 50/50 hexane:ethyl acetate | 240 | 8-9 | 78 |
| | | 10-14 | 160.1 |
| | | 15-16 | 58 |
| | | 17-18 | 72.2 |
| 100% ethyl acetate | 120 | 19-21 | 74.9 |
| | | 22-25 | 70.6 |
| 95:5:0.7 ethyl acetate-methanol-water | 120 | 26-28 | 156.4 |
| | | 29-31 | 50.5 |
| 83:17:1.4 ethyl acetate-methanol-water | 240 | 32-35 | 42.7 |
| | | 36-38 | 50.3 |
| | | 39 | 66.2 |
| | | 40 | 76 |
| | | 41-45 (A) | 132 |
| 67:33:2.5 ethyl acetate-methanol-water | 240 | 46-50 (B) | 72 |
| | | 51 | 77 |
| | | 52-55 | 209.5 |
| 50:50:5 ethyl acetate-methanol-water | | 56-60 | 56 |
| 45:45:10 ethyl acetate-methanol-water | | 61-65 | 100 |
| | | 66-69 | 30.5 |

Each fraction was eluted with 20 l of solvent and comparable (by TLC) fractions were combined Isolation of Dolastatin 13. From the preparative HPLC fractions, two displayed significant activity in the F388 system, fraction A (132.0 g PS T/C toxic→165 at 30→7.5 mg/kg and $ED_{50}$ $10^{-2}$ and fraction B (72.0 g, PS T/C toxic→141 at 35→8.7 mg/kg and $ED_{50}$ $10^{-2}$). The fractions were combined and dried to give 190.4 g. The major portion (152 g) was treated as shown below in Separation Schemes Part 1, Part 2, and Part 3.

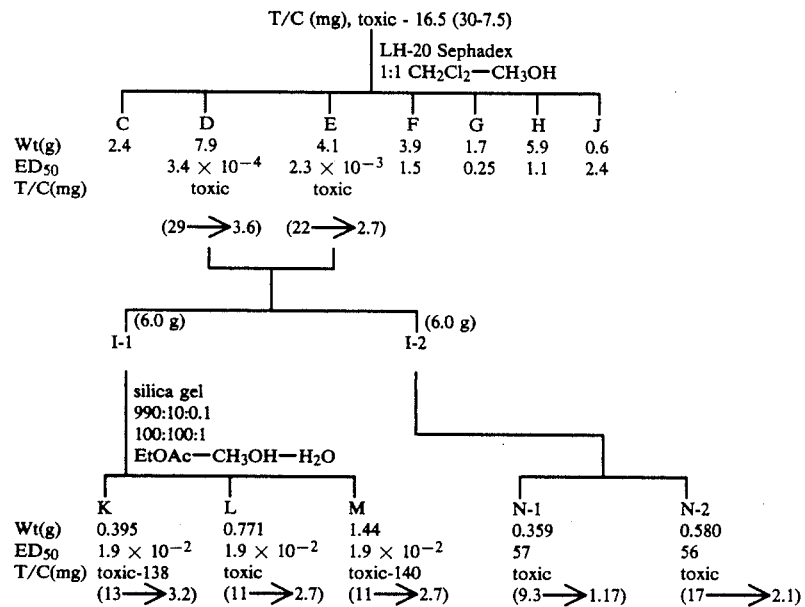
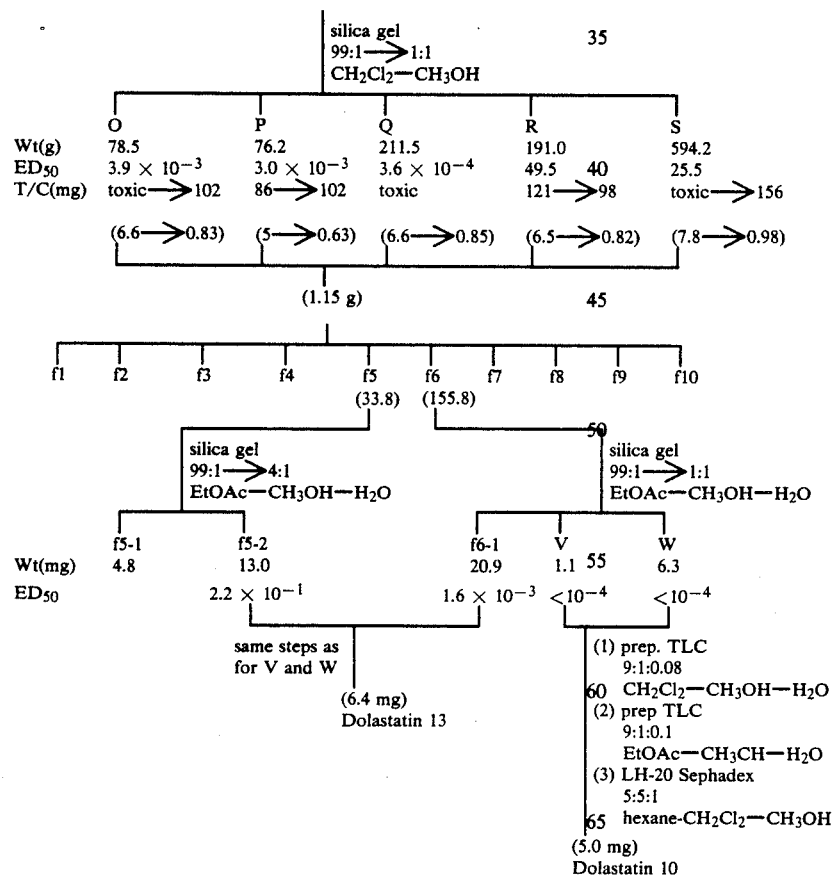

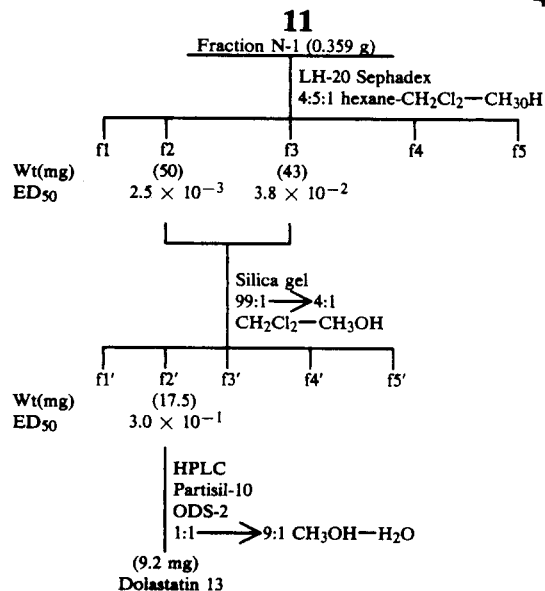
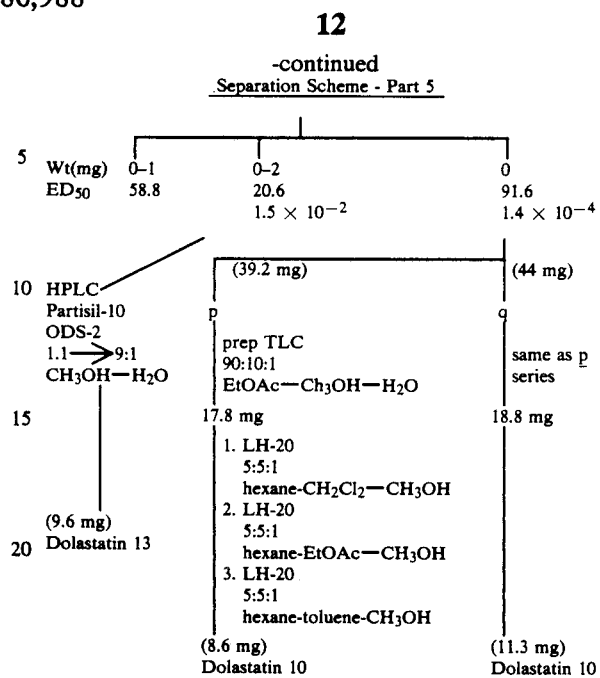
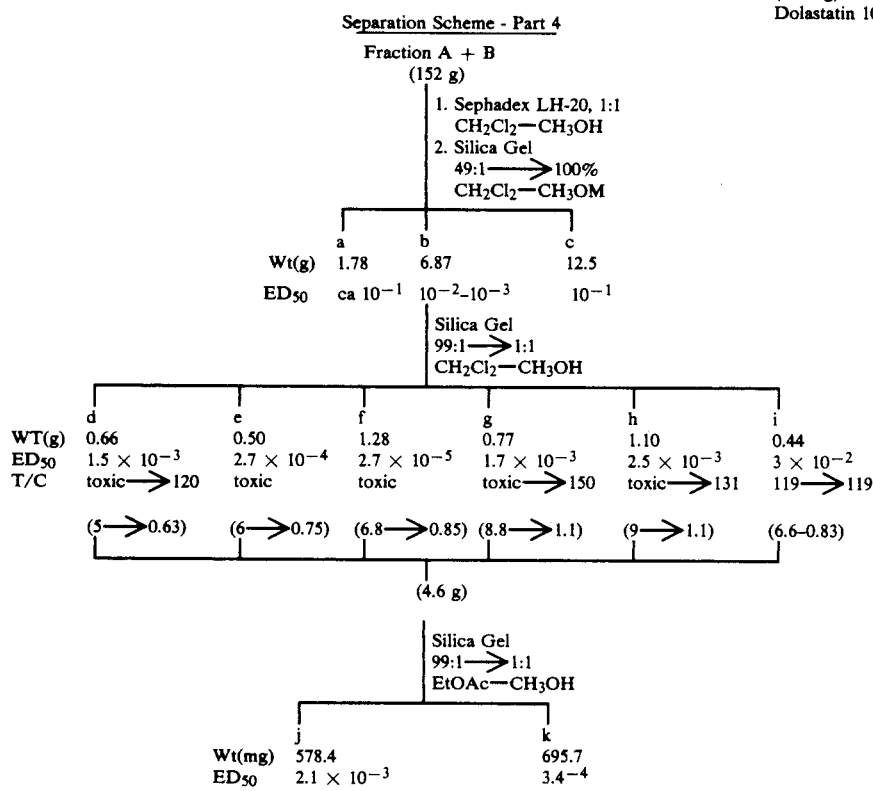
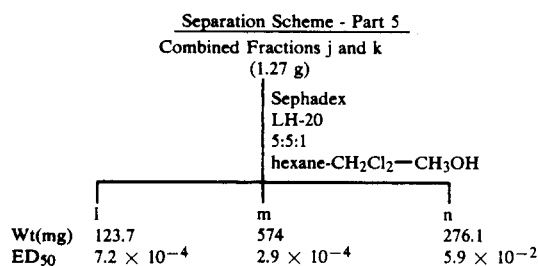

Isolation and Purification

A variety of methods can be used to isolate and purify dolastatin 13 and dehydrodolastatin 13 from samples of sea hare as previously indicated.

In a preferred practice of the present invention, a 38 gram sample of fraction A+B was chromatographed on a column of Sephadex LH-20 (10×120 cm) in 1:1 methylene chloride-methanol. Combination of similar fractions gave fractions C-3 as outlined in Separation Scheme Part 1, supra. The active (in vivo) fractions D and E were combined and divided into two equal parts (6.0 each) for separation using silica gel column chromatography. The I-1 series was further separated by dry column chromatography with a gradient of 990:10:0.1 to 100:100:1 ethyl acetate-methanol-water to give active fractions K, L, and M. The parallel I-2 series was also separated by dry column chromatography using methylene chloride-methanol and the gradient 99:1 to 1:1 giving active fraction N. Combined fractions K, L, M (2.6 g) were separated using dry column silica gel chromatography and a 99:1 to 1:1 methylene chloride-methanol gradient to give active fractions O-S (1.15 g) as detailed on Separation Scheme Part 2, supra. The combined active fractions O-S were then separated again on a column of silica gel, using a 99:1 to 4:1 methylene chloride-methanol gradient that resulted in 10 fractions (f1→f10). The fraction f6 (155.8 mg) was further separated on a column of silica gel (wet) using 99:1 to 1:1 ethyl acetate-methanol to give active fractions V and W, in addition to the fraction f6-1.

Combined V and W (7.4 mg) was finally separated by three steps including preparative TLC with 9:1:0.8 methylene chloride-methanol-water and again with 9:1:0.1 ethyl acetate-methanol-water followed by partition chromatography using SEPHADEX LH-20 and 5:5:1 hexane-methylene chloride as solvent. Thus, series I-1 led to 5.0 mg of dolastatin 10.

On the other hand, fraction f5 (33.8 mg) (part 2) was chromatographed with silica gel using 99:1 to 4:1 ethyl acetate-methanol-water (water: 0.1%) giving the fraction f5-2 (13 mg; $ED_{50}$ $2.2 \times 10^{-1}$) This fraction was combined with the fraction f6-1 (20.9 mg; $ED_{50}$ $1.6 \times 10^{-3}$) according to TLC analysis. Combined fractions f5-2 and f6-1 were finally separated in three steps following the same procedures as shown in Separation Scheme Part 5 for the separation of dolastatin 10 and yielded 6.4 mg of crystalline dolastatin 13 ($ED_{50}$ $1.3 \times 10^{-2}$).

Additional dolastatin 13 was obtained, beginning with the I-2 series in Part 1. Continuation of the separation with Series I-2 yielded fraction N-1 (0.359 g). LH-20 SEPHADEX partition separation with the 4:5:1 hexane-methylene chloride-methanol solvent system of the fraction N-1 gave two active fractions f2 and f3 as shown in Part 3. The combined fraction (93 mg) was chromatographed on a silican gel column with 99:1→4:1 $CH_2Cl_2$—$CH_3OH$ as solvent to give an active fraction f2 (17.5 mg). The HPLC separation with reverse phase (on PARTISIL-10, ODS-2) using 1:1→9:1 $CH_3OH$—$H_2O$ provided 9.2 mg of crystalline dolastatin 13.

The larger amount of fraction A+B (152 g) was chromatographed on columns (10×120 cm) of SEPHADEX LH-20 in five portions in 1:1 methylene chloride-methanol as described in Separation Scheme Part 1-3, supra. The active fractions were combined and further separated using a column (4.5×80 cm; 1.2 kg) of silica gel and a stepwise gradient of methylene chloride-methanol (49:1 23:2, 9:1, 22:3, 17:3, 4:1, 1:1 and lastly, 100% methanol) to give active fraction b (6.87 g). Fraction b was rechromatographed on silica gel (dry) using a 99:1 to 1:1 methylene chloride-methanol gradient. The resulting active fractions d-i (4.6 g) were combined and chromatographed (dry column) on silica gel using a 99:1 to 1:1 ethyl acetate-methanol gradient to give active fractions j and k (1.27 g).

Two fractions (j and k combined) were chromatographed on SEPHADEX LH-20 using a 5:5:1 hexane-methylene chloride-methanol partition system to afford active fraction m. Separation of fraction m on silica gel (Size B Merck prepack) with a 99:1 to 1:1 methylene chloride-methanol gradient procedure gave active fractions 0–1 (58.8 mg), 0–2 (20.6 mg) and 0 (91.6 mg), respectively.

At this point, fraction 0 was used in two parts. Fractions p and q were purified separately in parallel using preparative TLC (90:10:1 ethyl acetate-methanol-water mobile phase) followed by successive SEPHADEX LH-20 partition steps with 5:5:1 hexane-methylene chloride-methanol, 5:5:1 hexane-ethyl acetate-methanol and lastly the 5:5:1 hexane-toluene-methanol solvent system. Fraction p gave 8.6 mg and fraction q gave 11.3 mg of pure dolastatin 10: total yield, 28.7 mg of amorphous (colorless) powder (mp 107°–112°) from methylene chloride-methanol.

Active fraction 0–2 (20.6 mg; $ED_{50}$ $1.5 \times 10^{-2}$) was separated by reverse phase HPLC (ODS-2) with 1:1→9:1 $CH_3OH$—$H_2O$ to give 9.6 mg (crystals) of dolastatin 13.

Separation of strongly active fraction 1 on silica gel (Size B, Merck prepack) employing a 99:1 to 1:1 methylene chloride-methanol gradient procedure gave active fraction f4 (12:8 mg; $ED_{50}$ $7.2 \times 10^{-4}$) as shown in Separation Scheme Part 3. The resulting active fraction was finally separated using HPLC (silica gel ODS-2 column) with a 1:1 to 9:1 methanol-water gradient. By this procedure, 6.2 mg of pure dolastatin 13 was obtained.

The structure of dolastatin 13 has been illustrated at page 9, and the spectral and HMBC correlations are shown in Table I at pages 11 and 12.

The administration of dolastatin 13, the related hydrodolastatin 13, its synthetic counterparts, and their pharmaceutically active, physiologically compatible derivatives is useful for treating animals or humans bearing a neoplastic disease associated with malignant cell growth, for example, acute myelocytic leukemia, acute lymphocytic leukemia, malignant melanoma, adenocarcinoma of lung, neuroblastoma, small cell carcinoma of lung, breast carcinoma, colon carcinoma, ovarian carcinoma, bladder carcinoma, and the like.

The dosage administered will be dependent upon the identity of the neoplastic disease; the type of host involved, including its age, health and weight; the kind of concurrent treatment employed, if any; the frequency of treatment and therapeutic ratio.

Illustratively, dosage levels of the administered active ingredients are: intravenous, 0.1 to about 20 mg/kg; intramuscular, 1 to about 50 mg/kg; orally, 5 to about 100 mg/kg; intranasal instillation, 5 to about 100 mg/kg; and aerosol, 5 to about 100 mg/kg. As used herein, mg/kg means weight of active ingredient in milligrams divided by the body weight of the host in kilograms.

Expressed in terms of concentration, an active ingredient can be present in the compositions of the present invention for localized use about the cutis, intranasally, pharyngolaryngeally, bronchially, intravaginally, rectally, or ocularly in a concentration of from about 0.01% to about 50% w/w of the composition; and for parenteral use in a concentration of from about 0.05% to about 50% w/v of the composition and preferably from about 5% to about 20% w/v.

The compositions of the present invention are preferably presented for administration to humans and animals in unit dosage forms, such as tablets, capsules, pills, powders, granules, suppositories, sterile parenteral solutions or suspensions, sterile non-parenteral solutions or suspensions, oral solutions or suspensions and the like, all of which contain suitable quantities of the active ingredient.

For oral administration either solid or fluid unit dosage forms can be prepared.

Powders are prepared quite simply by comminuting the active ingredient to a suitably fine size and mixing it with a similarly comminuted diluent. The diluent can be an edible carbohydrate material such as lactose or starch. Advantageously, a sweetening agent or sugar and a flavoring oil will be present.

Capsules are produced by preparing a powder mixture as described above and filling the mixture into formed gelatin sheaths. As an adjuvant to the filling operation, a lubricant such as a talc, magnesium stearate, calcium stearate and the like can be added to the powder mixture before the filling operation.

Soft gelatin capsules are prepared by machine encapsulation of a slurry of active ingredient disposed in an acceptable vegetable oil, light liquid petrolatum or other inert oil or triglyceride.

Tablets are made by preparing a powder mixture as described above, granulating or slugging the powder, adding a lubricant and pressing the resulting mixture into tablets. The powder mixture is prepared by mixing an active ingredient, suitably comminuted, with a diluent or base such as starch, lactose, kaolin, dicalcium phosphate and the like. The powder mixture can be granulated by wetting with a binder such as corn syrup, gelatin solution, methylcellulose solution or acacia mucilage and forcing the bound mixture through a screen. As an alternative to granulating, the powder mixture can be slugged, i.e., run through the tablet machine and the resulting imperfectly formed tablets broken into pieces (slugs). The slugs can be lubricated to prevent sticking to the tablet-forming dies by means of the addition of stearic acid, a stearic salt, talc or mineral oil. The lubricated mixture is then compressed into tablets.

When desired, each tablet can be provided with a protective coating consisting of a sealing coat or enteric coat of shellac, a coating of sugar and methylcellulose and a polish coating of carnauba wax.

Fluid unit dosage forms for oral administration such as syrups, elixirs and suspensions can be prepared wherein each teaspoonful of composition contains a predetermined amount of active ingredient for administration. The water-soluble forms can be dissolved in an aqueous vehicle together with sugar, flavoring agents and preservatives to form a syrup. An elixir is prepared by using a hydroalcoholic vehicle with suitable sweeteners together with a flavoring agent. Suspensions can be prepared of the insoluble forms with a suitable vehicle with the aid of a suspending agent such as acacia, tragacanth, methylcellulose and the like.

For parenteral administration, fluid unit dosage forms are prepared utilizing an active ingredient and a sterile vehicle, water being preferred. The active ingredient, depending on the form and concentration used, can be either suspended or dissolved in the vehicle. In preparing solutions the water-soluble active ingredient can be dissolved in water for injection and filter sterilized before filling into a suitable vial or ampule and sealing. Advantageously, adjuvants such as a local anesthetic, preservative and buffering agents can be dissolved in the vehicle. Parenteral suspensions are prepared in substantially the same manner except that an active ingredient is suspended in the vehicle instead of being dissolved and the sterilization procedure can not be accomplished by filtration. The active ingredient can be sterilized by exposure to ethylene oxide before suspending in the sterile vehicle. Advantageously, a surfactant or wetting agent is included in the composition to facilitate uniform distribution of the active ingredient throughout the vehicle.

In addition to oral and parenteral administration, the rectal and vaginal routes can be utilized as effective delivery systems. Thus the active ingredient can be administered by means of a suppository. A vehicle which has a melting point at about body temperature or one that is readily soluble can be utilized. For example, cocoa butter and various polyethylene glycols (Carbowaxes) can serve as the vehicle.

For intranasal instillation, a fluid unit dosage form is prepared utilizing an active ingredient and a suitable pharmaceutical vehicle, preferably pyrogen free ("P.E.") water. A dry powder can be formulated when insufflation is the administration of choice.

For use as aerosols, the active ingredients can be packaged in a pressurized aerosol container together with a gaseous or liquefied propellant, for example, dichlorodifluoromethane, carbon dioxide, nitrogen, propane, and the like, with the usual adjuvants such a cosolvents and wetting agents, as may be necessary or desirable.

The term "unit dosage form" as used in the specification and claims refers to physically discrete units suitable as unitary dosages for human and animal subjects, each unit containing a predetermined quantity of active material calculated to produce the desired therapeutic effect in association with the required pharmaceutical diluent, carrier or vehicle. The specifications for the novel unit dosage forms of this invention are dictated by and are directly dependent on (a) the unique characteristics of the active material and the particular therapeutic effect to be achieved, and (b) the limitation inherent in the art of compounding such an active material for therapeutic use in humans, as disclosed in this specification, these being features of the present invention. Examples of suitable unit dosage forms in accord with this invention are tablets, capsules, troches, suppositories, powder packets, wafers, cachets, teaspoonfuls, tablespoonfuls, dropperfuls, ampules, vials, segregated multiples of any of the foregoing, and other forms as herein described.

The active ingredients to be employed as antineoplastic agents can be easily prepared in such unit dosage form with the employment of pharmaceutical materials which themselves are available in the art and can be prepared by established procedures. The following preparations are illustrative of the preparation of the unit dosage forms of the present invention, and not as a limitation thereof.

EXAMPLE I

Several dosage forms were prepared embodying the present invention. They are shown in the following examples in which the notation "active ingredient" signifies dolastatin 13, its related dehydrodolastatin 13, their synthetic counterpart and the non-toxic pharmaceutically active derivatives thereof.

COMPOSITION "A"

Hard-Gelatin Capsules

One thousand two-piece hard gelatin capsules for oral use, each capsule containing 20 mg of an active ingredient are prepared from the following types and amounts of ingredients:

| Active ingredient, micronized | 20 gm |
|---|---|
| Corn Starch | 20 gm |
| Talc | 20 gm |
| Magnesium stearate | 2 gm |

The active ingredient, finely divided by means of an air micronizer, is added to the other finely powdered ingredients, mixed thoroughly and then encapsulated in the usual manner.

The foregoing capsules are useful for treating a neoplastic disease by the oral administration of one or two capsules one to four times a day.

Using the procedure above, capsules are similarly prepared containing an active ingredient in 5, 25 and 50 mg amounts by substituting 5 gm, 25 gm and 50 gm of an active ingredient for the 20 gm used above.

COMPOSITION "B"

Soft Gelatin Capsules

One-piece soft gelatin capsules for oral use, each containing 20 mg of an active ingredient (finely divided by means of an air micronizer), are prepared by first suspending the compound in 0.5 ml of corn oil to render the material capsulatable and then encapsulating in the above manner.

The foregoing capsules are useful for treating a neoplastic disease by the oral administration of one or two capsules one to four times a day.

COMPOSITION "C"

Tablets

One thousand tablets, each containing 20 mg of an active ingredient are prepared from the following types and amounts of ingredients.

| Active ingredient micronized | 20 gm |
|---|---|
| Lactose | 300 gm |
| Corn starch | 50 gm |
| Magnesium stearate | 4 gm |
| Light liquid petrolatum | 5 gm |

The active ingredient finely divided by means of an air micronizer, is added to the other ingredients and then thoroughly mixed and slugged. The slugs are broken down by forcing through a Number Sixteen screen. The resulting granules are then compressed into tablets, each tablet containing 20 mg of the active ingredient.

The foregoing tablets are useful for treating a neoplastic disease by the oral administration of one or two tablets one to four times a day.

Using the procedure above, tablets are similarly prepared containing an active ingredient in 25 mg and 10 mg amounts by substituting 25 gm and 10 gm of an active ingredient for the 20 gm used above.

COMPOSITION "D"

Oral Suspension

One thousand ml of an aqueous suspension for oral use, containing in each teaspoonful (5 ml) dose, 5 mg of an active ingredient, is prepared from the following types and amounts of ingredients:

| Active ingredient micronized | 1 gm |
|---|---|
| Citric acid | 2 gm |
| Benzoic acid | 1 gm |
| Sucrose | 790 gm |
| Tragacanth | 5 gm |
| Lemon Oil | 2 gm |
| Deionized water, q.s. 1000 ml | |

The citric acid, benzoic acid, sucrose, tragacanth and lemon oil are dispersed in sufficient water to make 850 ml of suspension. The active ingredient finely divided by means of an air micronizer, is stirred into the syrup until uniformly distributed. Sufficient water is added to make 1000 ml.

The composition so prepared is useful for treating a neoplastic disease at a dose of 1 tablespoon (15 ml) three times a day.

COMPOSITION "E"

Parenteral Product

A sterile aqueous suspension for parenteral injection, containing in 1 ml, 30 mg of an active ingredient for treating a neoplastic disease, is prepared from the following types and amounts of ingredients:

| Active ingredient, micronized | 30 gm |
|---|---|
| Polysorbate 80 | 5 gm |
| Methyparaben | 2.5 gm |
| Propylparaben | 0.17 gm |
| Water for injection, q.s. 1000 ml | |

All the ingredients, except the active ingredient, are dissolved in the water and the solution sterilized by filtration. To the sterile solution is added the sterilized active ingredient, finely divided by means of an air micronizer, and the final suspension is filled into sterile vials and the vials sealed.

The composition so prepared is useful for treating a neoplastic disease at a dose of 1 milliliter (1M) three times a day.

COMPOSITION "F"

Suppository, Rectal and Vaginal

One thousand suppositories, each weighing 2.5 gm and containing 20 mg of an active ingredient are prepared from the following types and amounts of ingredients:

| Active ingredient, micronized | 1.5 gm |
|---|---|
| Propylene glycol | 150 gm |
| Polyethylene glycol #4000, q.s. | 1,500 gm |

The active ingredient is finely divided by means of an air micronizer and added to the propylene glycol and the mixture passed through a colloid mill until uniformly dispersed. The polyethylene glycol is melted and the propylene glycol dispersion added slowly with stirring. The suspension is poured into unchilled molds at 40° C. The composition is allowed to cool and solidify and then removed from the mold and each suppository is foil wrapped.

The foregoing suppositories are inserted rectally or vaginally for treating a neoplastic disease.

COMPOSITION "G"

Intranasal Suspension

One thousand ml of a sterile aqueous suspension for intranasal instillation is prepared, containing 20 mg of an active ingredient per ml of suspension, from the following types and amounts of ingredients:

| | |
|---|---:|
| Active ingredient, micronized | 1.5 gm |
| Polysorbate 80 | 5 gm |
| Methylparaben | 2.5 gm |
| Propylparaben | 0.17 gm |

All the ingredients, except the active ingredient, are dissolved in the water and the solution sterilized by filtration. To the sterile solution is added the sterilized active ingredient, finely divided by means of an air micronizer, and the final suspension is aseptically filled into sterile containers.

The composition so prepared is useful for treating a neoplastic disease, by intranasal instillation of 0.2 to 0.5 ml given one to four times a day.

An active ingredient can also be present in the undiluted pure form for use locally about the cutis, intranasally, pharyngolaryngeally, bronchially, or orally.

COMPOSITION "H"

Powder

Five grams of an active ingredient in bulk form is finely divided by means of an air micronizer. The micronized powder is placed in a shaker-type container.

The foregoing composition is useful for treating a neoplastic disease, at localized sites by applying a powder one to four times per day.

COMPOSITION "I"

Oral Powder

Ten grams of an active ingredient in bulk form is finely divided by means of an air micronizer. The micronized powder is divided into individual doses of 20 mg and packaged.

The foregoing powders are useful for treating a neoplastic disease, by the oral administration of one or two powders suspended in a glass of water, one to four times per day.

COMPOSITION "J"

Insufflation

Ten grams of an active ingredient in bulk form is finely divided by means of an air micronizer.

The foregoing composition is useful for treating a neoplastic disease, by the inhalation of 30 mg one to four times per day.

COMPOSITION "K"

Hard Gelatin Capsules

One hundred two-piece hard gelatin capsules for oral use, each capsule containing 20 mg of an active ingredient.

The active ingredient is finely divided by means of an air micronizer and encapsulated in the usual manner.

The foregoing capsules are useful for treating a neoplastic disease, by the oral administration of one or two capsules, one to four times a day.

Using the procedure above, capsules are similarly prepared containing active ingredient in 5, 25 and 50 mg amounts by substituting 5 gm, 25 gm and 50 gm of the active ingredient for the 20 gm used above.

EXAMPLE 2

Unit dosage forms of dolastatin 13 prepared according to selected compositions described in Example I were screened utilizing Protocol 1,200 described in *Cancer Chemotherapy Reports.* part 3, Vol. 3, No. 2, September 1972, pp 9 et seq for lymphocytic leukemia P388 and provided positive results. Dolastatin 13 also markedly inhibited growth of the P388 in vitro cell line ($ED_{50} = 1.3 \times 10^{-2}$ μg/ml).

From the foregoing it becomes readily apparent that new and useful linear depsipeptides having cell growth inhibitory powers, new and useful cytostatic preparations, and new and useful therapeutic regimens have been herein described and illustrated which fulfill all of the aforestated objectives in a remarkably unexpected fashion. It is of course understood that such modifications, alterations and adaptations as will readily occur to the artisan confronted with this disclosure are intended within the spirit of the present invention which is limited only by the scope of the claims appended hereto. Accordingly,

What is claimed is:

1. A cell growth inhibitory substance denominated dolastatin 13 having the structural formula:

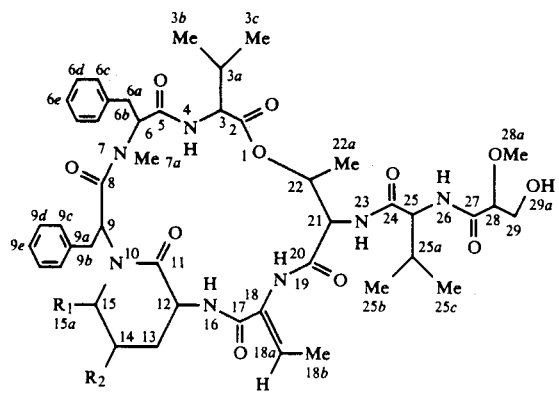

wherein: $R_1 = OH$; $R_2 = H$.

2. A cell growth inhibitory substance denominated dehydrodolastation 13 having the structural formula:

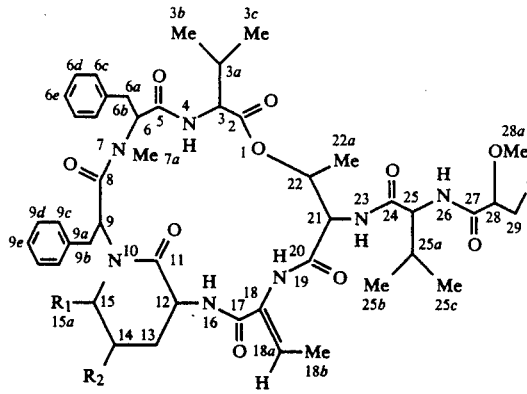

wherein: $R_1 = R_2 = \Delta^{13,15}$.

3. A pharmaceutical preparation comprising a pharmaceutically acceptable carrier and an amount effective to inhibit cell growth of a natural or synthetic substance or a non-toxic pharmaceutically active derivative thereof, said substance having the structural formula:

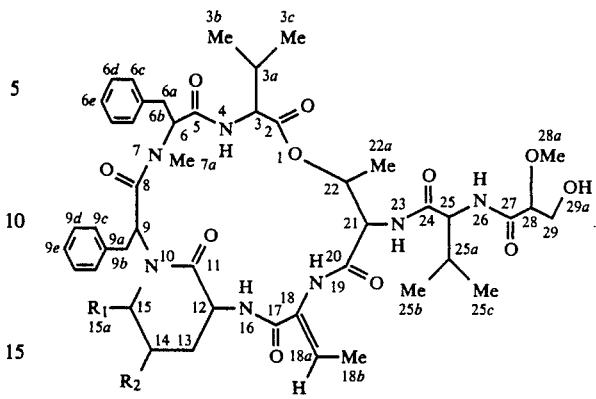

wherein: $R_1 = OH$; $R_2 = H$.

4. A pharamaceutical preparation comprising a pharmaceutically acceptable carrier and an amount effective to inhibit cell growth of a natural or synthetic substance or a non-toxic pharmaceutically active derivative thereof, said substance having the structural formula:

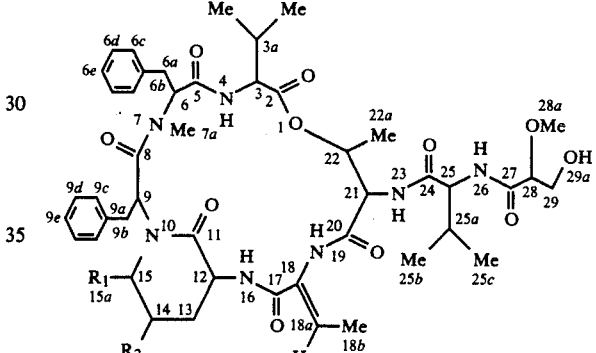

wherein: $R_1 = R_2 = \Delta^{14,15}$.

* * * * *